United States Patent [19]

Dodman

[11] Patent Number: 5,762,960
[45] Date of Patent: *Jun. 9, 1998

[54] VETERINARY METHOD FOR CLINICALLY MODIFYING THE BEHAVIOR OF DOGS EXHIBITING CANINE AFFECTIVE AGGRESSION USING PREFERENTIAL/ DISCRIMINATORY SEROTONIN REUPTAKE INHIBITORS

[75] Inventor: Nicholas H. Dodman, Grafton, Mass.

[73] Assignee: Trustees of Tufts College, Medford, Mass.

[*] Notice: The term of this patent shall not extend beyond the expiration date of Pat. No. 5,554,383.

[21] Appl. No.: 677,796

[22] Filed: Jul. 10, 1996

Related U.S. Application Data

[63] Continuation-in-part of Ser. No. 417,747, Apr. 6, 1995, Pat. No. 5,554,383.

[51] Int. Cl.$^6$ .............. A61F 2/02; A61K 9/127; A61K 9/20; A61K 31/44
[52] U.S. Cl. .............. 424/451; 424/423; 424/427; 424/430; 424/434; 424/450; 424/464; 424/489; 514/288; 514/315; 514/415
[58] Field of Search .............. 424/451, 423, 424/427, 430, 434, 450, 464, 489; 514/288, 315, 415

[56] References Cited

U.S. PATENT DOCUMENTS 5,554,383  9/1996  Dodman .............. 424/451

*Primary Examiner*—Carlos Azpuru
*Attorney, Agent, or Firm*—David Prashker

[57] ABSTRACT

A veterinary method for clinically modifying the behavior of a household pet dog exhibiting a recognized type of canine affective aggression behavior is provided. The veterinary behavior modification method administers at least one preferential serotonin reuptake inhibitor compound to the dog upon one or multiple occasions; and the administration of these compounds will modify clinically the canine affective aggression behavior of the household dog permanently or for an indefinite period of time. This veterinary behavior modification method can be usefully employed as an adjunct to conditioning approaches presently employed and will avoid the need for euthanasia in extreme behavioral circumstances.

7 Claims, 1 Drawing Sheet

PLEASE CHECK THE APPROPRIATE BOX IF YOUR DOG EXHIBITS ANY OF THE LISTED BEHAVIORS AT ANY TIME WHEN YOU OR ANY MEMBER OF THE FAMILY DO THE FOLLOWING:

| | GROWL | LIFT LIP | SNAP | BITE | NO AGGRESIVE RESPONSE | TRIED |
|---|---|---|---|---|---|---|
| TOUCH DOG'S FOOD WHILE EATING | | | | | | |
| WALK PAST DOG WHILE EATING | | | | | | |
| ADD FOOD WHILE DOG IS EATING | | | | | | |
| TAKE AWAY REAL BONE OR RAWHIDE | | | | | | |
| WALK BY DOG WHEN S/HE HAS A REAL BONE/RAWHIDE | | | | | | |
| TOUCH DELICIOUS FOOD WHEN DOG IS EATING | | | | | | |
| TAKE AWAY A STOLEN OBJECT | | | | | | |
| PHYSICALLY WAKE DOG UP | | | | | | |
| PHYSICALLY DISTURB DOG | | | | | | |
| RESTRAIN DOG WHEN IT WANTS TO GO SOMEPLACE | | | | | | |
| LIFT DOG | | | | | | |
| PET DOG | | | | | | |
| MEDICATE DOG | | | | | | |
| HANDLE DOG'S FACE/MOUTH | | | | | | |
| HANDLE DOG'S FEET | | | | | | |
| TRIM THE DOG'S TOENAILS | | | | | | |
| GROOM DOG | | | | | | |
| BATHE OR TOWEL OFF | | | | | | |
| TAKE OFF OR PUT ON COLLAR | | | | | | |
| PULL DOG BACK BY THE COLLAR OR SCRUFF | | | | | | |
| REACH FOR GRAB DOG BY THE COLLAR | | | | | | |
| HOLD DOG BY THE MUZZLE | | | | | | |
| STARE AT THE DOG | | | | | | |
| REPRIMAND DOG IN LOUD VOICE | | | | | | |
| VISUALLY THREATEN DOG: NEWSPAPER OR HAND | | | | | | |
| HIT THE DOG | | | | | | |
| WALK BY DOG IN CRATE | | | | | | |
| WALK BY/ TALK DOG ON FURNITURE | | | | | | |
| REMOVE DOG FROM FURNITURE PHYSICALY OR VERBALLY | | | | | | |
| MAKE DOG RESPOND TO COMMAND | | | | | | |

PLEASE CHECK THE APPROPRIATE BOX IF YOUR DOG EXHIBITS ANY OF THE LISTED BEHAVIORS AT ANY TIME WHEN YOU OR ANY MEMBER OF THE FAMILY DO THE FOLLOWING:

| | GROWL | LIFT LIP | SNAP | BITE | NO AGGRESIVE RESPONSE | TRIED |
|---|---|---|---|---|---|---|
| TOUCH DOG'S FOOD WHILE EATING | | | | | | |
| WALK PAST DOG WHILE EATING | | | | | | |
| ADD FOOD WHILE DOG IS EATING | | | | | | |
| TAKE AWAY REAL BONE OR RAWHIDE | | | | | | |
| WALK BY DOG WHEN S/HE HAS A REAL BONE/RAWHIDE | | | | | | |
| TOUCH DELICIOUS FOOD WHEN DOG IS EATING | | | | | | |
| TAKE AWAY A STOLEN OBJECT | | | | | | |
| PHYSICALLY WAKE DOG UP | | | | | | |
| PHYSICALLY DISTURB DOG | | | | | | |
| RESTRAIN DOG WHEN IT WANTS TO GO SOMEPLACE | | | | | | |
| LIFT DOG | | | | | | |
| PET DOG | | | | | | |
| MEDICATE DOG | | | | | | |
| HANDLE DOG'S FACE/MOUTH | | | | | | |
| HANDLE DOG'S FEET | | | | | | |
| TRIM THE DOG'S TOENAILS | | | | | | |
| GROOM DOG | | | | | | |
| BATHE OR TOWEL OFF | | | | | | |
| TAKE OFF OR PUT ON COLLAR | | | | | | |
| PULL DOG BACK BY THE COLLAR OR SCRUFF | | | | | | |
| REACH FOR GRAB DOG BY THE COLLAR | | | | | | |
| HOLD DOG BY THE MUZZLE | | | | | | |
| STARE AT THE DOG | | | | | | |
| REPRIMAND DOG IN LOUD VOICE | | | | | | |
| VISUALLY THREATEN DOG: NEWSPAPER OR HAND | | | | | | |
| HIT THE DOG | | | | | | |
| WALK BY DOG IN CRATE | | | | | | |
| WALK BY/ TALK DOG ON FURNITURE | | | | | | |
| REMOVE DOG FROM FURNITURE PHYSICALY OR VERBALLY | | | | | | |
| MAKE DOG RESPOND TO COMMAND | | | | | | |

FIG. 1

VETERINARY METHOD FOR CLINICALLY MODIFYING THE BEHAVIOR OF DOGS EXHIBITING CANINE AFFECTIVE AGGRESSION USING PREFERENTIAL/ DISCRIMINATORY SEROTONIN REUPTAKE INHIBITORS

CROSS-REFERENCE

This application is a Continuation-In Part of U.S. patent application Ser. No. 417,747 filed Apr. 6, 1995, now U.S. Pat. No. 5,554,383.

FIELD OF THE INVENTION

The present invention is concerned generally with the veterinary treatment of animal behavioral problems commonly found in human family households; and is particularly directed to the veterinary clinical modification of affective aggression behaviors expressed by domesticated dogs kept as household pets.

BACKGROUND OF THE INVENTION

Veterinary pharmacology in general is not an easy subject to master because of the multiplicity of species concerned. The veterinarian is asked to care for the health of the entire animal kingdom with the exception of humans. Thus, the experienced veterinarian must constantly remind himself to be alert to the fact that various species of animals may respond differently to certain drugs. These major differences in reaction among the animal species to either a single drug and/or a particular class of drugs are the essence of veterinary pharmacology as distinguished from human medical pharmacology [*Veterinary Pharmacology and Therapeutics*, 6th edition, (Nicholas H. Booth and Leslie E. MacDonald, editors), Iowa State University Press, 1988, Chap. 1, p. 7].

In this context, it will also be recognized and appreciated that clinical modification of undesirable animal behaviors exhibited by household domesticated pets using psychopharmacological agents is a relatively new phenomenon in veterinary medicine and today is a most-poorly understood therapy among practicing veterinarians. Prior to about 1974, the veterinary science of modifying specific animal behaviors was in its most rudimentary stages; and the idea of pharmacologically treating specific behavior problems in domesticated animals or household pets was in its infancy. Subsequently, between about 1974–1984, such animal behavior modification methods as existed focused primarily upon behavioral shaping technique developed from the science of ethology, the study of innate animal behavior patterns; and employed conditioning strategies to elicit behavior modifications in the animal. Thus, the use of pharmacologically active substances to control or modify undesired animal behaviors was only just being explored in the mid-1980s and was seen as a most radical and suspect approach by most practicing veterinarians. Moreover, after 1985 and continuing even to date for most veterinarians, the idea of administering psychopharmacological agents to household pets as a means for clinically modifying undesirable animal behaviors was and remains directly comparable and analogous to the skepticism of clinicians and attending physicians of human medicine at about 1950 who found ever the concept of treating humans exhibiting behavioral disorders with psychopharmacological drugs to be a rash and unwholesome idea.

Moreover, in direct contradistinction to the human condition and the human patient suffering from a mental disorder like anxiety, domesticated animals such as the household dog cannot and do not verbally complain of mental ailments such as an agitated or a stressed state of mind. Thus, household dogs do not speak subjectively of "anxiety", or "depression", or "aggressive feelings"; cannot verbalize or describe symptoms either as a psychological problem or a social interaction phenomenon; and cannot communicate with human veterinarians directly in any decipherable manner. Household dogs are veterinary subjects, and as such can only display observable manifestations either of normal or of disturbed or unusual behaviors. In addition, because household dogs cannot speak about their state of mind or explain themselves to the practicing veterinarian, it is only the observed animal behavioral condition and specific animal conduct which can be identified and clinically determined to be a recognized type of behavior problem.

The human condition and the pharmacological treatment of the various human mental states, however, do provide a somewhat skewed, historical background and context-particularly as concerns psychotropic drugs intended for human usage. It is desirable, therefore, summarily to review here the range of human aggressive behaviors, their underlying psychological mental disorders, and the development of psychopharmacological methods for controlling the various acts of human aggression insofar as it may pertain to or aid in understanding the practicing veterinarian's dilemma.

The Human Condition

Human acts performed with the deliberate intent of causing physical harm to persons or property are, by definition, human aggression; and such aggressive acts have a wide range of causative factors. Moreover, human aggressive behaviors and human acts of violence are considered symptoms rather than diseases and are most frequently associated with an underlying psychological disorder rather than a medics condition. Thus depression, schizophrenia, personality disorders, mania, paranoia, temporal lobe dysfunction, and the consequences of substance abuse each may be the underlying disorder associated with one or more specific acts of human aggression. [*Current Medical Diagnosis & Treatment* 1995 Tierney, McPhee and Papadakis, editors, Appleton & Lange, Norwalk, Conn.; Maxmen, J. S. and N. G. Ward, *Essential Psychopathology And Its Treatment*, Second edition, W.W. Norton & Co., 1995.]

It is also noteworthy that human psychopharmacology as a science and the continuing search for the origins and mediators of human aggressive behaviors in its many different forms and varieties have been related areas of investigation since the late 1940s. Clinical concerns with treating highly aggressive human individuals were initially and remain today a starting point for inquiries into the range of neurobiological mechanisms that cause, mediate, or control human aggressive behavior patterns; and, within the clinical setting, human aggression is seen as an abnormality, a psychopathological or sociopathological behavior pattern that requires therapeutic intervention.

Human psychopharmacology and human neuropharmacology in particular have evolved and developed in major part as a response to the ongoing need for a range of different agents which can be used in the treatment of diverse pathological aggressive behaviors or for controlling the differing symptoms of aggression and hostility that are part of human pathological behavioral disorders. A host of human affective mental disorders (including mood disorders such as major depression and bipolar mania and psychotic disorders such as schizophrenia) often include violent behaviors and aggressive outbursts which may be treatable using particular classes of psychopharmacological drugs. In comparison, pathological aggressive behavioral ac based upon neural mechanisms, or the intense aggressive behavior exhibited in the course of human addiction to and withdrawal from narcotics—each may require very different classes of psychopharmaceutical agents as therapeutic treatments [Yudofsky et. al., *Psychiatric Annals* 17:397–407 (1987)].

Many different forms of human aggressive behavior are individually known and well characterized either by reports of personal case medical histories or by human experimental-psychological group studies. Due to ethical considerations, however, humans are not suitable candidates for clinical or research experimentation. For these reasons, experimental procedures and settings were designed during the 1960s and 1970s for the purpose of generating a range and variety of animal models which might be representative and illustrative of specific types or selected examples of human aggressive behaviors and/or serve as an indicator for the underlying root causes and mediators of human aggressive behaviors. Thus, almost every major class of psychopharmacological drugs intended for human usage has been investigated in different animal models, each representative of a specified type of human aggressive behavior. These models were conducted mainly in isolated mice and rats that were exposed to pain or other stimuli, but also utilized fish, pigeons, cats and primates as representative subjects. [See for example: Sheard, M. H., "Animal Models Of Aggressive Behavior" in *Animal Models In Psychiatry And Neurology*, Pergamon Press Oxford, 1977, pp. 247–257; Eichelman, B., "Animal models: Their role in the aggressive behavior of humans", *Progr. Neuro-Psychopharmacol.* 2:633–643 (1978); and Miczek, K. A., "The Psychopharmacology Of Aggression" in *HANDBOOK OF PSYCHOPHARMACOLOGY*, Vol. 19, Plenum Publishing Corp., 1987, Chap. 4, pp. 183–328 and the references cited therein.]

Representative Animal Model Paradigms

A summary review of the various types or categories of different animal models often used as representative examples of human behaviors provides insight and understanding as to their intrinsic limitations and substantive restrictions. One animal model experimental design employs exposure to aversive living conditions to engender aggressive behavior. In these model experiments, deprivation of social contact, or crowding and restricted access to limited resources such as food, or the presentation aversive external stimuli such as electric shock pulses and omission or intermittency scheduled reinforcement—are used as artificial and experimental manipulations to intentionally induce and elicit aggressive behaviors in the test animals. All of these a environmental manipulations and are usually performed upon placid and domesticate laboratory animals which rarely exhibit aggressive behavior. Thus, in this animal model system, to evoke or induce an act of aggression by intentionally exposing an otherwise non-aggressive animal subject to aversive environmental stimuli has led to the often expressed view that aggressive behavior represents an antisocial response. [See for example: Malick, J. B., *Curr. Der. Psychopharmacol.* 5:1–27 (1979); Oliver et al, Psychopharmacology 97:154–156 (1989); Krsiak, M., *Res. Commun. Chem. Path. Pharmacol.* 7:253–257 (1974); Oliver, B. and D. von Dalen, *Aggress. Behav.* 8:163–168 (1982).]

A second kind of animal model system uses direct electrical or chemical stimulation of neural foci to evoke sequences of attack and defense behaviors as well as predatory attack in several animal species. In this model system, electrical neuronal activity is detected and often recorded; and the brain stimulation evoked aggressive or defensive behaviors exhibited by the animals is said to parallel in many respects the animal behavior seen in the wild or under natural conditions. [See for example: Siege et. al., *Brain Res.* 93:473–484 (1975); Yamamoto et. al., *Jpn. J. Pharmacol.* 29:(Supp) 41P (1979); Conner et. al. *Physiol. Behav.* 5:1221–1224 (1970).]

Another animal model of human aggressive behaviors begins with the premise that every living species (human or animal) that can fight will fight, given the appropriate conditions. Thus, in this animal model system, an attack toward a territorial intruder or towards an unfamiliar group member; or a defense of one's young; or the competition for preferred food, mates, and niches of living; or a threat in the context of change in group formation and social standing—all are aggression provoking situations. These diverse types or forms of aggressive behaviors have collectively been termed "agonistic behaviors" in order to capture under one general heading the many different behavior elements typically encountered among these diverse conflict situations. [See for example: Scott, J. P., *Aggression*, University of Chicago Press, 1958; Scott, J. P., *Am. Zoologist* 6:683–701 (1966); Dixon, A. K. and H. P. Kaesermann, "Ethopharmacology of flight behavior," in *Ethopharmacology Of Agonistic Behavior In Animals And Humans*, Martinus Nijhoff, Dordrecht, 1987, pp. 46–70.]

In addition, as human aggressive behaviors became increasingly recognized as being of differing types and causes; and that a single type of human aggressive behavior may be pathological, or antisocial; the reported scientific investigations of neural mechanisms of action for aggression and therapeutic agent interaction have generated highly varied differences and sometimes even contradictions in information and knowledge. These reported experimental differences, empirical discrepancies, evidentiary inconsistencies, and conclusionary contradictions are often the consequence of intrinsic differences in the overall investigative strategy chosen for use. Traditionally, two different investigative strategies have been pursued. A first type (I) of research study uses drugs as tools for identifying and characterizing the neural mechanisms that might underlie a specific kind of aggressive behavior. This first type (I) assumes that the mechanism of drug action is well understood; and thus the experimental results are a direct reflection and consequence of specific drug interactions—a questionable premise. Alternatively, the second type (II) of investigative strategy employs specific aggressive acts as a means to screen for evaluating a novel compound or class of drugs; or to serve as markers for a specific neurotransmitter, a specific neurotransmitter activity, or a neurotransmitter receptor protein. The underlying premise and assumption of these second type (II) investigations is that the selected aggressive behavior and its neural basis are known, well understood, and adequately described in the literature.

Unfortunately, it is generally now appreciated that the in-vivo mechanisms for even the simplest aggressive act and behavior are very complex and incompletely understood. Any type of aggression and aggressive behavioral action must be carefully characterized and individually distinguished as to specific origin, type and nature. The scientific literature is replete with reviews and classification frameworks describing, separating, and distinguishing among the many forms of behavioral aggression. Merely representative of such publications are the following, the texts of which are each expressly incorporated by reference herein: Maxmen, J. S. and N. G. Ward, *Essential Psychopathology And Its Treatment*, Second edition, W. W. Norton & Co., 1995;

HANDBOOK OF PSYCHOPHARMACOLOGY (Iversan et. al., editors), Vol. 19, 1987, Plenum Publishing Corp., Chap. 4, pp. 183–328; Drews, C., "The Concept And Definition Of Dominance In Animal Behavior", Behavior 125: 286–313 (1993); Miczek, K. A. and P. Donat, "Brain 5-HT System And Inhibition Of Aggressive Behavior", in BEHAVIORAL PSYCHOPHARMACOLOGY OF 5-HT (Bevan, Cools & Archer, editors), 1989, Lawrence Erlbaum Associates, Chap. 10, pp. 117–144].

Neurotransmitter Models And Theories

Equally important today in understanding properly the behavioral complexities of aggression behaviors and aggressive interactions is the now generally discredited theory and erroneous view that modifications of a single neurotransmitter might yield meaningful changes in aggressive behavior. It is important to note that at varying times in the history of this technological field, each of the known endogenous biogenic amines present in the brain and/or neural tissue was suspected of being the critical "code" or key to controlling and modifying aggressive behavior. Thus, in turn, the "aggressive monoamines" [Eichelman et. al., Pharmacol. Biochem. Rev. 1: 121–123 (1973)], hypothalamic acetylcholine [Smith et. al., Science 167: 900–901 (1970)], and serotonin [Valzelli, L. and S. Grattini, Adv. Pharmacol. 6B: 249–260 (1968)] each were offered and wrongly presented as being mediators in the control of all aggressive behavior. About 1970, the single neurotransmitter theory of control was expanded initially to a "neurochemical dualism" and then eventually increased to a theory of multitransmitter control of aggressive behaviors. [See for example: Reis, D. J., "The chemical coding of aggression in brain" in Neurohumoral Codina Of Brain Function, 1974, Plenum Press, pp. 125–150; Avis, H. H., Psychol. Bull. 81: 47–63 (1974); Pradhan, S. N., "Aggression And Central Transmitters" in International Review Of Neurobiology, 1975, Academic Press, p. 213; Daruna, J. H., Neurosci. Biobehav. Rev. 2: 101–113 (1978)]. Within these theories, just as a nerve cell membrane may either be excited of inhibited at the cellular level, aggressive behavior was wrongly believed to be under to excitatory and inhibitory control by functionally opposite neurotransmitters. The candidates for such behavioral mediation were thought to be initially norepinephrine and acetylcholine, which were later supplanted by dopamine and serotonin. This concept of exciting and inhibiting aggressive behavior by opposing neurotransmitters is seen today as overly simplistic and unable to account for the origins, range, and diversity of aggressive human behaviors as well as failing to explain or account for the behavioral complexities of aggressive interactions among members of the same species, much less between individuals of different species. [See for example: Miczek, K. A., "The Psychopharmacology of Aggression," in Handbook of Psychopharmacology, (Ivarsan et. al., editors), Plenum Pub. Co., Vol. 19, 1987, Chap. 4, pp. 183–328 and the references cited therein.]

With the discrediting of the "code" neurotransmitter theories for controlling all human aggression behaviors generally, the recent trends of research investigations and psychopharmacological experimentation in this field have begun to explore what might be the actual function of the various endogenous neurotransmitters and the true nature of their interactions in specific kinds of human aggressive behaviors, often using carefully selected animal models representative of a specific type of human aggression. These more recently published reports have typically followed one of two different investigative themes: Evaluations of active neurotransmitters and/or neurotransmitter metabolites in living human patients suffering from specific and well characterized forms of aggression; and purposeful challenges of neurotransmitters and/or their receptors within selected animal models putatively representative of a specific human aggressive behavior.

Exemplifying the investigations of neurotransmitters and their metabolites with human patient pools exhibiting a specified form of aggressive behaviors are the following publications: Serotonin in obsessions, compulsions and aggressive impulses of man [Insel et. al., Ann. N.Y. Acad. Sci. 487:574–582 (1987)]; biological correlates of suicidal risk and aggressive behavior traits in man [Linnoila, M. and M. Virkkunen, J. Clin. Psychopharmacol. 12:19S–20S (1992)]; central serotonin and impulsive aggression in man [Coccaro, E. F., Brit. J. Pysch. 155:52–62 (1989)]; serotonin, suicide, and aggression in man [Golden et. al., J. Clin. Psych. 52:61–69 (1991)]; relationships between central and peripheral serotonin indexes in depressed and suicidal psychiatric inpatients [Mann et. al., Arch. Gen. Psychiatry 49:442–446 (1992)]; the relationship of tryptophan, 5-HIAA, and IAA to sex, age, epilepsy and anticonvulsive drugs [Young et. al., J. Neurol. Neurosurci. Psych. 43:438–445 (1980)]; CSF neurochemistry in depressed, manic and schizophrenic human patients compared to human normal controls [Gurner et. al., Am. J. Psych. 141:1533–1540 (1984)]; suicidality and 5-HIAA concentration associated with the tryptophane hydroxylase gene in man [Nielsen et. al. Arch. Gen Psychiatry 51:34–38 (1994)]; personality profiles and state aggressiveness in Finnish alcoholic, violent offenders, fire setters, and healthy volunteers [Virkkunen et. al., Arch. Gen Psychiatry 51:28–33 (1994)]; serotonin correlates of suicidal and aggressive behaviors in man [Coccaro, E. F. and R. J. Kavoussi, Neuropsychopharmacology 10:726S–727S (1994)]; and the role for central 5-HT receptor function in impulsive aggressive behavior in humans [Coccaro et. al., Psychopharmacology Bulletin 26:393–405 (1990)].

In comparison, the investigations of neurotransmitters, their metabolites, and chemical challenges of these within controlled animal models representative of a specific human aggression behavior are merely illustrated by the following publications reconciling the role of central serotonin neurons in human and animal behavior using rats [Soubrie, P., The Behavior And Brain Sciences 9:319–364 (1986)]; relationship between dominance hierarchy, cerebrospinal fluid levels of amine transmitter metabolites (5-HIAA and homovanillic acid) and plasma control in monkeys [Yodyingyuard et. al., Neuroscience 16:851–858 (1985)]; hormone-dependent aggression in male and female rats [Albert et. al., Neurosci. Biobehav. Rev. 15:177–192 (1992)]; the increase of serotonin but not dopamine metabolites in brain regions of subordinate rats in a colony [Blanchard et. al., Brain Res. 568:61–66 (1991)]; the reversal of testosterone-induced dominance by the serotonergic agonist quipazine between male rat pairs [Bonson, K. R. and J. C. Winter, Pharmacology Biochemistry and Behavior 42:809–813 (1992)]; effects of monoaminergic agonists on alcohol-induced increases in mouse aggression [Wagner et. al., J. Stud. Alcohol. Supp. 11:185–191 (1993); serotonergic control of anabolic steroid-induced aggression in rats [Bonson et al., Pharmacology Biochemistry and Behavior 49:313–332 (1994)]; aggressive behavior in mice lacking 5-HT$_{1B}$ receptor [Saudou et. al., Science 265:1875–1878 (1994)]; serotonergic mechanisms promoting dominance aggression in adult male vervet monkeys [Raleigh et. al., Brain research 559:181–190 (1991)]; prolactin responses to fenfluramine challenge in adult male cynomolgus macaques [Botchin et. al., Neuropsychopharmacology 9:93–99 (1993)]; the role of brain serotonin neurons in dominance-subordination behavior among rats [Kotowski et. al., Physiol. Behav. 33:365–371 (1984)]; and inherent and environmental factors influencing serotonergic activity and behavior in monkeys [Kaplan et. al., Neuropharmacology 10:389S (1994)].

The Tricyclic Dibenzazerine Derivatives

The substituted dibenzazepines are a family of tricyclic compounds exemplified by imipramine and clomipramine (substituted dibenzazepine derivatives) amitriptyline and nortriptyline (substituted dibenzocycloheptadiene derivatives), doxepin (a dibenzoxepine derivative) and protriptyline (a dibenzocycloheptatriene). This family of tricyclic compositions originated in the late 1940s when imipramine was first synthesized and investigated as a therapeutic drug on the basis of its sedative or hypnotic properties. During clinical investigation, it was found that imipramine, although relatively ineffective in quieting agitated psychotic human patients, instead bestowed remarkable benefits upon human patients suffering from severe depression [Kuhn, R., Am. J. Psychiatry 115: 459–464 (1958)]. Since then, indisputable evidence for the effectiveness of this family of compounds in alleviating human depression has accumulated [Klerman, G. L., J Psychiatr. Res. 9: 253–270 (1972); Hollister, L. E., N Engl. J. Med. 299: 1106–1109 and 1168–1172 (1978)]. For this reason primarily, this family of compositions have become conventionally known in human medicine as the "tricyclic antidepressants".

All the presently known tricyclic dibenzazepine derivatives are believed to be effective in the treatment of human depression in its various recognized forms. Among these are the major depression episodes which imply a prominent and relatively persistent depression or dysphoric mood that usually interferes with human daily functioning and includes at least five of the following nine symptoms: depressed mood, markedly diminished interest or pleasure in all or almost all activities; significant weight loss or gain when not dieting or a decrease or increase in appetite; insomnia or hypersomnia; psychomotor agitation or retardation; fatigue or loss of energy; feelings worthlessness or excessive or inappropriate guilt; diminished ability to think or concentrate or indecisiveness; recurrent thoughts of death, suicidal ideation or suicidal attempts [Drug Facts and Comparison, 1995 edition, page 1384].

Since all of the members of this dibenzazepine derivative family each have a three-ring molecular core and each produces effective responses in most human patients suffering from major depression, the trivial name "tricyclic antidepressants" has been used for this category of drugs. Thus, all the tricyclic antidepressant compositions have a common and very similar chemical structure. Moreover, from a biochemical point of view, the major differences among them is to be found on the individual side chain, some compounds being N-dimethylated (imipramine) while others are N-monomethylated (desipramine). These differences are, however, merely arbitrary, since the dimethylated drugs are metabolized in-vivo into the monomethylated structures. Thus, for example, the administration of clomipramine leads to a therapeutic effect by both the initial dimethylated and intermediate monomethylated substances [Balant-Gorgia et al., Clin. Pharmacokinet 20: 447–462 (1991) and the references cited therein].

For human therapeutic uses, the tricyclic family of dibenzazepine derivatives (in their various formulations and structures) are utilized primarily for treatment of human depression. Among the nine or ten homologues and analogs comprising this family of compositions, clompramine [ANAFARNIL] has been available for many years in a number of countries for the treatment of human depression; and it is one of the most widely used tricyclic antidepressants in Western Europe. In some other countries, notably the U.S., clompramine has only recently been approved for the treatment of particular human mental conditions such as obsessive compulsive disorders [McTavish D. and P. Benfield, Drugs 39: 136–153 (1990)].

It will be recognized and appreciated, however, that the major pharmacological property and characteristic for a tricyclic antidepressant is its sedative potential. Thus the primary benefit of the drug, the intended therapeutic effect, and desired result for the human patient suffering from depression are to sedate or tranquilize the person in a calmer and more restful state of mind. For this reason, a ranking order for the sedative potential or strength for the commonly used formulations has been empirically determined. It is difficult, if not impossible, however, to rank the different tricyclic antidepressant compounds in terms of their clinical efficacy, since in all well designed double-blind comparative clinical trials they show almost identical profiles. It is thus proper to state that clomipramine has an efficacy and side-effect profile in line with those of the other tricyclic antidepressants comprising the family; and its wide use in some countries and not in others is representative of the local, and often historical, reasons that determine the choice of one compound's usage over the others in the same family [Balant-Gorgia, et al., Clin. Pharmacokinet. 20: 447–462 (1991)]. Thus, clomipramine has gained recognition as a favored therapeutic drug for: treatment of humans suffering from obsessive compulsive disorder, depressive illness and resistant depression [Trimble, M. R., J. Clin. Psychiatry. 51: 8 (Supp.) (1990)]; for treatment of autistic disorder in humans [Gordon et al., Arch. Gen. Psychiatry 50: 441–447 (1993)]; and for the treatment of trichotillomania, a related disorder of obsessive compulsive human behavior [Rappaport, J. L., Neuropsychopharmacology 5: 1–10 (1991)].

Veterinary Uses Of Tricyclic Antidepressants

The scientific literature of the United States has shown only a very limited interest in veterinary applications of the tricyclic antidepressants as a family. Representative of the reported clomipramine usages in the U.S. is the treatment of canine acral lick dermatitis in certain large breeds of dogs such as Labrador Retrievers German Shepards, Great Danes and St. Bernards [Rapopart et al., Arch. Gen. Psychiatry 49: 517–521 (1992)]; and the inclusion of tricyclic antidepressants such as clomipramine in pharmacologic approaches to managing different behavioral problems in a variety of small animals [Dodman, N. H. and L. Shuster, Veterinary Medicine October, 1994, pp. 960–969].

A very different perspective, however, has been presented by veterinarians in France. These have followed the published views and position taken by Patrick P. Pageat as outlined and delineated in his published remarks presented to the National Conference of Veterinarians Specializing in Small Animals, May 30, 1991. The Pageat/French point of view is that anxiety belongs to a category of emotional disorders; and that the "normal" emotional responses and emotional behaviors must be clinically recognized in order to treat emotional disorders in the domesticated dog. The impulsive and non-deliberative behaviors controlled by the autonomous nervous system of the dog constitute the emotional responses; and these emotional responses are characterized by a display of physiologic reactions which include tachycardia, tachypena, hyper-intestinal peristalsis, expulsion of the anal glands, urinating in small quantities, vomiting, sweating, and the like. Behaviorially, three levels of emotional responses will appear: apprehension; fear; and emotional shock. When these emotional reactions occur occasionally and in corresponding appropriate circumstances, they are considered normal and do not require veterinary treatment. However, if these emotional responses are observed irregularly or spontaneously irreversibly under ordinary circumstances, these reactions signify an emotional disorder in the animal.

The emotional disorders are defined by Pageat as intermittent or occasional modifications of the animal's emotional status outside any typically provocative context. Three modifications and emotional disorders of clinical status exist: phobia; anxiety; and depression. These animal emotional disorders thus represent veterinary equivalents of and parallels to known human psychiatric conditions and disorders [as defined in *Diagnostic and Statistical Manual of Psychiatry* (Vol. IV)].

The Pageat treatment of anxiety, an emotional disorder, in the domesticated carnivore (dogs and cats) utilizes a variety of anxiolytics or tranquilizing substances previously employed for the treatment of mental anxiety in humans. However, an explicit warning is given in advance by Pageat to the veterinarian: Before prescribing any anxiolytic substance for the veterinary treatment of anxiety in a domesticated animal, it must be remembered that anxiolytics are strictly contra-indicated for subjects who have shown aggressive behavior.

Presuming therefore that no aggressive behavior as such is shown or has been observed for the animal having an emotional disorder, the preferred anxiolytics (or tranquilizers) for use are benzodiazepines; beta-blockers; "morpholines"; and neuroleptics. The use of antidepressant drugs, however, is quite limited. The tetracyclic antidepressant "mianserine" may be co-administered together with the morpholine "trioxazine" to achieve a type of euphoric effect; and the tricyclic antidepressant clomipramine may be employed as a sedative when concurrently administered in combination with a neuroleptic such as "pipamperone" [Pageat, P., C.N.V.S.P.A., 30 Mai 1991].

The Pageat doctrine and chemotherapeutic approach has been generally embraced by French veterinarians as proper veterinary approach and treatment for: agonistic behaviors of aged cats and dogs where aging induces physiological and pathological mechanisms for behavioral modifications, especially pertubations of the agonistic behaviors of self-defense [Dehasse, J., Congres annuel du CNVSPA, 1991]; aggressive-agonistic behaviors in aging animals [Gay-Bataile, B., *Semaine veterinaire*, no. 615, 4 Mai 1991]; pathological anticipatory defense behavior in dogs [Dehasse, J., *B.V.C.E.* Vol. 2, no. 3/4, Nov. 1994]; behavioral pathologies in dogs and the drugs for their treatment [Pageat, P., Ed Point Vetereinaire, 1995]; and troubles for the dog in the hierarchy of the family pack [Muller, G., Action Veterinaire, no. 1325, 12 Mai 1995].

Among the range of veterinary behavioral disorders (which may include some forms of overt aggressive conduct), the chemotherapeutic drugs directed for use are the neuroleptics such as pipamperone or levopromazine; the thymoregulators such a valpromide; and beta-blockers such as propronolol. If the animals' behavior requires sedation, an antidepressant such as clomipramine may be concurrently administered in combination with the neuroleptic or thymoregulator substance. However, if aggressive behavior is seen, the use of anxiolytics such as benzodiazepines (which increase aggressiveness and decrease memory) remains contra-indicated and is to be avoided.

It will be noted and appreciated, nevertheless, that among these French publications and the veterinary practice and doctrine presented by Dr. Pageat draws a distinct and unwavering difference and delineation between anxiety and an anxious state of mind in an animal and aggressive behavior and aggression in domesticated animals. The favored chemotherapeutic approach to treatment of anxiety and an anxious state in the animal is via the use of anxiolytic drugs or tranquilizing substances such as benzodiazepines; alternatively, beta-blockers; morpholines, and some psychotropic drugs are used. Most preferred, however, are the classes of drugs known as "neurolepics" and "thymoregulators". In addition, if the animal is in a highly excitable or anxious state, it is often desirable to utilize a sedative or tranquilizing agent in combination with one or more of the preferred non-anxiolytic substances. For this specific purpose, clomipramine is said to be a favored adjunct sedative agent and is to be used only in combination with the primary treatment drug such as a neuroleptic drug, e.g. pipamperone. Thus, while the neuroleptic substance (pipamperone) serves to alleviate the anxious state of mind and reduce mental anxiety, the adjunctive and concurrent use of clomipramine provides sedation for the animal by providing a calming effect. These combination therapies are strictly limited, however, to the anxious state of mind and the treatment of "anxiety" in the domesticated animal.

It is explicitly stated and emphasized repeatedly in the French veterinary literature, however, that no anxiolytic substance should be given to a domesticated animal showing any form of overt aggression. The prohibition and warning is explicit: all anxiolytics or anxiolytic substances are strictly contraindicated for veterinary subjects who have shown aggressive behavior. The French veterinary practice as reported in essence has therefore taken the following position: if the domesticated animal is in an anxious state of mind and shows symptoms of "anxiety" the appropriate chemotherapeutic treatments include the use of neuroleptics; thymoregulator substances; or a recognized anxiolytic drug. Also, if the animal is found to be in a highly emotional state, concurrent administration of a sedative or tranquilizing agent as an adjunct therapy to calm the animal may be given, the sedative agent of choice being clomipramine. In the alternative situation, if the domesticated animal shows aggressive behavior or manifestations of aggression as part of the observed clinical state, the use of benzodiazepines or other anxiolytic substances is explicitly contra-indicated. In general, therefore, the French veterinary practice appears extrapolated from and corresponds meaningfully to the conventional human therapeutic uses for the tricyclic substituted dibenzazepines—i.e., solely as sedative or tranquilizing agents to calm excitability or depression in the living subject. The historical overview presented herein thus reveals that the various animal models have been and remain today a primary research investigative tool used for the betterment of humans and human problems; and that even today there is much which is not yet understood about the actions of active psychopharmacological agents and their effects upon the various forms of human behavior disorders. Equally important, as limited as the comprehension is today regarding the complexity of human psychopharmacological treatments for specific forms of human aggression behaviors, the quantum of knowledge and information directed to veterinary behavioral problems and a purposeful veterinary use of psychopharmacological agents for clinically modifying a varied range of animal behaviors is far more circumscribed and far less reliable. Accordingly, the generation and clinical demonstration of an effective veterinary psychopharmaceutical treatment method clinically to modify specified forms of animal affective aggression behaviors in a household pet would be viewed as an unforeseen development, unusual benefit and marked advantage by practicing veterinarians.

SUMMARY OF THE INVENTION

The present invention is a veterinary method for clinically modifying the behavior of a household dog exhibiting a type of canine affective aggression. This veterinary behavioral modification method comprises steps of:

administering to the household dog exhibiting a type of canine affective aggression behavior an effective amount of at least one preferential serotonin reuptake inhibitor compound; and allowing sufficient time for said administered preferential serotonin reuptake inhibitor compound to modify clinically the canine affective aggression behavior of the household dog.

BRIEF DESCRIPTION OF THE FIGURES

The present invention may be more easily and completely understood when taken in conjunction with the accompanying drawing in which FIG. 1 is a canine overt aggression score chart employed experimentally.

DETAILED DESCRIPTION OF THE METHODOLOGY

The present invention is a unique clinical treatment method for modifying the observed behavior of a household dog which exhibits a characterized type of canine affective aggression behavior. Another behavioral modification process suitable for domesticated dogs exhibiting a recognized type of affective aggression is the subject matter of U.S. patent application Ser. No. 417,747 filed Apr. 6, 1995 and utilizes exclusively the class of pharmacologically active compositions known as "selective serotonin uptake inhibitors." However, in addition to this prior category of active and effective compounds, a functionally related but entirely different and chemically distinguishable alternative category of pharmacologically active compositions has now been identified which are also effective individually and collectively in modifying the behavior of household dogs displaying canine affective aggressive behaviors. The suitability of this second unique category of pharmacologically active compounds for this clinical purpose is an entirely unknown and unforeseen development.

The present invention thus is a veterinary method pertinent to the observed behavior and purposeful treatment of animal behavior and is not merely a theoretical study of particular canine behaviors. To the contrary, as will be described in detail hereinafter, this veterinary method pertains to a readily identifiable category of dog behaviors termed "canine affective aggression behaviors"; and serves to modify clinically the undesired behavior of a household dog which exhibits a recognizable type of canine affective aggression. This veterinary behavior modification method provides multiple advantages and unexpected benefits which include the following:

1. The present veterinary method serves to modify the behavior of pet dogs suffering from canine affective aggression, the problem most commonly presented to practicing veterinarians. Because of the risks to human family members, the dog owners, as well as other persons, such forms of aggressive behavior are a source of intense emotional conflict for the dog owners and often have led to euthanasia of the pet. The present methodology provides a therapeutic alternative for modifying the undesirable and troublesome behavior of the pet dog; and will serve to diminish, if not entirely eliminate, the need for euthanasia as a means of resolution for these canine behaviors.

2. The present veterinary methodology can be utilized as a complete or a partial alternative to conventional techniques for modifying canine affective aggression behaviors in a household dog pet. Traditional approaches to behavior modification are limited and have employed conditioning techniques such as a withdrawal of attention, obedience training, the use of collars and leads, the avoidance of gratuitous petting or solicitousness, the use of fencing or other physical barriers, and calming exercises. The present invention may thus be initially employed as an adjunctive therapy in combination with the conventionally employed conditioning techniques. However, in more severe instances and disruptive behaviors, a greater reliance and use of the pharmacological methodology will provide major changes in dog behavior and a modification of decreasing aggression which is sustained for an indefinite period of time. Thus, the present invention may be used exclusively or in combination with conventional conditioning techniques in an adjunctive role which may itself be major or minor in duration and effect.

3. The present veterinary method may be employed over a wide range of time usages. Although a single dosage and treatment occasion may be partly effective in as little as a week's time, this is the least desirable mode of practicing the present invention. Instead, it is desirable that the method for modifying clinically the behavior be used in multiple dose and treatment occasions; be continued for 4–5 weeks duration once it has been initiated in order to obtain a major change of behavior in the household dog; and preferably will be extended for 26 months duration or even longer in order to obtain a permanent modification and change of behavior in the pet.

4. The veterinary methodology employs at least one preferential serotonin reuptake inhibitor compound, of which a well characterized range of membership is presently known and commercially available. The methodology thus permits a choice of one or more psychopharmacological agents whose specific properties and side effects may be individually matched to fit the age, general health, and personal characteristics of the household pet undergoing treatment. This range of choices and variety of active agents thus provides both the practicing veterinarian and the human owners of the dog with some degree of latitude and flexibility in choosing the dose schedule and the preferred route of administration in order to obtain a desired modification and meaningful change in the behavior of the dog.

I. CLASSES AND TYPES OF VETERINARY AGGRESSION

A. Primary Classes And Various Categories Of Veterinary Aggression.

Veterinary aggression generally has been classified and divided into two main categories: predatory aggressive behaviors and affective aggressive behaviors [Reis, D., Neurosurg. 18:471–502 (1971)]. Predatory aggression is innate, reflexive behavior triggered by moving prey (or perceived prey). This category of veterinary aggression involves minimal mood changes and is believed to be an automatic and preprogrammed form of behavior. Often, the term "instinctive behavior" is utilized as a reference to this class of veterinary aggression.

Affective aggression, on the other hand, is characterized by a marked mood change as well as by autonomic nervous system (sympathetic) activation which results in pupillary dilation and piloerection. Affective aggression can be offensive or defensive in form, depending on the inciting or initiating events. The animal's posture and the circumstances of his aggressive behavior often help distinguish between offensive and defensive behaviors.

Canine affective aggression behaviors are the problem most commonly presented to practicing veterinarians for treatment [Beaver, B. V., *Appl. Anim. Ethol.* 10:35–43 (1983)]. Due to the risks of injury to either the human family members who keep the dog as a household pet or to human strangers who are invited or incidentally intrude into the family household, affective aggression behaviors are a source of intensive emotional conflict for dog owners.

It is most important also to recognize and appreciate some of the differing indici and attributes of canine affective aggression behavior which separate and distinguish the class as an individual and distinct category from other veterinary behaviors. These class differences include the following:

(1) Canine effective aggression behaviors are considered to be norirnal behavior for dogs generally; and as such are not pathological, diseased, abnormal or irregular veterinary states or medical conditions. The Nobel prize winner Conrad Lorenz in his book *On Aggression* [Harcourt, Brace & World, NY, 1958] points out that affective aggression is so ubiquitous in the animal kingdom that it must be properly viewed as a normal behavior; and this is the traditional view accepted by ethologists today. It is therefore normal behavior for dogs to use the language of aggression to ensure continuing stability in their pack; and it is normal for a dog to react fearfully to fear-inducing stimulus with the classical reaction of aggressive behavior. Similarly, it is also normal for a dog to defend its territory using aggressive behavior as the means for defense. Thus, in the process of dealing with each of these incidents or contingencies the dog's behavior becomes noticeably changed and more aggressive during the encounter; and this observed change to aggressive behavior is both expected and normal. This is what is termed "canine affective aggression."

(2) This category of observed animal behavior does not include or encompass abnormal aggressive behaviors arising from structural brain disease, biochemical disorders, or cognitive dysfunctions. Specifically excluded from affective aggression behaviors is: aggression resulting from congenital brain anomalies such a hydrocephalus; aggression resulting from traumatic brain injury; aggression resulting from infectious causes (e.g., rabies); aggression secondary to brain tumors or brain seizure activity; aggression resulting from hormonal problems or imbalances (e.g., hypothyroidism); aggression resulting from allergy; aggression resulting from nutritional toxic or metabolic causes; and aggression resulting from cognitive dysfunction syndrome (a veterinary form of senile dementia or Alzheimer's Disease) which has been recently identified in dogs.

(3) Canine affective aggression behavior also does not constitute or embrace the functional psychoses as such. These psychoses are disorders of the mind which result in abnormal (exaggerated or diminished) responsiveness to environmental stimuli; Functional psychoses include panic disorders; specific phobias such as social phobias; obsessive-compulsive disorder; post-traumatic stress disorder; acute stress disorder; generalized anxiety disorders; anxiety due to a underlying general medical condition; and pharmacologically-induced anxiety disorders. Note also that although the various anxiety disorders may coexist or occur concurrently with aggressiveness in the same animal, they are not one and the same thing. Each clinical condition is separate and distinct from the other; the causes of functional psychoses are quite different from the origins of affective aggression; and the treatments for functional psychoses vary markedly from treatments intended for canine affective aggression behaviors.

(4) It is most important also to recognize and appreciate that canine affective aggression behavior—as a category of veterinary behavior—is radically different and completely unrelated to "affective aggression disorders in human psychiatry" which typically concern themselves with mental depression and mania as abnormal, irregular, and deviant human responses to the realities of every day life [See for example, *Current Medical Diagnosis & Treatment* 1986 (Krupp et. al., editors), Lange Medical Publications, pp. 670–673]. There is, therefore, no analogy or similarity, directly or indirectly, between human depression and human anxiety or anxious mental states and canine affective aggression behaviors.

B. Recognized Types Of Canine Affective Aggression Behaviors.

Within the broad class encompassing canine affective aggression behaviors as a whole, a range of different types of representative behaviors are known and individually identifiable. [The Friskies Symposium On Behavior, Apr.; 17, 1994, Friskies Petcare Co. and the School of Veterinary Medicine, University of California, Davis]. Among them are those canine affective aggression behaviors which involve humans as the recipients of aggressive advances. This specific type of canine affective aggression behaviors is thus termed interspecies aggression—a term which describes interactions between two different species, e.g. dogs and humans. In contrast, affective aggression in which the dog's behavior is directed against a member of the same species is termed interspecies aggression (i.e., dog versus dog interactions).

Most representative of the interspecies type of canine affective aggression behaviors are those described below.

Dominance-related aggression behavior:

Dominant-aggressive dogs exhibit growling, snarling or biting toward their owners and other familiar people. While each individual is unique, such dogs tend to act aggressive in the following circumstances:

1. When protecting food (dog food or human food), garbage, and certain objects (toys, stolen objects).
2. If disturbed while sleeping or resting, especially in socially significant areas such as furniture.
3. When a certain, closely bonded family member is approached or touched by other family members.
4. When they feel certain actions "threaten" their status. This can include certain postures such as bending over the dog, prolonged staring, punishment, pulling by the leash or collar, or even petting.

Dominance-related aggression may emerge in puppyhood, though dogs usually begin to exhibit serious aggression near the age of social maturity (1 to 3 years).

Territorial aggression behavior:

Territorial aggression is distinguished from dominance aggression by the target: while dominant-aggressive dogs direct threats to human family members, territorial dogs direct aggression towards human strangers. The natural tendency to sound an alarm when someone unfamiliar enters the home is exaggerated in some dogs. Territorial aggression is often a conditioned (learned) behavior, aggravated by long periods of unsupervised time within view of passersby. Aggressive barking, growling and biting threats can be exhibited in the home, yard, car or any area in which the dog has spent time (particularly with its family). Some dogs will threaten all who approach the owner while being walked on a lead. Such behavior is most pronounced in the socially mature dog (1 to 3 years), after which it tends to plateau. However, more severe aggression can be conditioned at any time. Males may be slightly more likely than females to exhibit territorial behavior. Any breed can be presented, though some are clearly predisposed (e.g. German Shepherd, Rottweiler, Kuvasz).

Fear-based aggression behavior:

Defensive or fear-based aggression can be displayed toward either family members or unfamiliar people. Owners may elicit a fear-related growl or bite when punishing their pets. Such behavior may be difficult to distinguish from dominance-related aggression without a detailed history of circumstances and postures assumed by the dog. Like dominance, fearfulness tends to be exhibited as a behavioral profile. Mildly affected dogs may threaten the source of their fear only in extreme circumstances, as during a veterinary visit; severely affected dogs may respond to more subtle threats. Such dogs often attempt to avoid threats, and will bite only when cornered or otherwise directly confronted. Fear-based aggression may be displayed by either sex, at any age. All breeds are affected; severely fearful dogs can be either genetically predisposed or environmentally conditioned (or both).

Aggression behavior directed toward children:

For understandable reasons, aggression behavior directed toward children in the home is particularly upsetting to dog owners. Dogs targeting children may be motivated by fear (e.g. due to lack of familiarity or memory of pain), or dominance. While adults may follow "rules" necessary for safety, toddlers and small children cannot be trusted to be consistent. Regardless of motivation for aggression, biting dogs should be leashed (attached to the owner) or actively supervised, muzzled or crated in the presence of small children. Aggressive behavior, which in some households may be regarded as mild, is potentially more dangerous in a home with children. Because of the natural transgressions of children, prevention of problems (as distinct from treatment) should be emphasized in such homes.

II. THE PRESENT VETERINARY BEHAVIOR MODIFICATION METHODOLOGY

The methodology as a whole is intended to be practiced by veterinarians who are presented with a household pet by the human owners with the compliant that the dog has been either disobedient, overtly aggressive, or actually attacked or injured a human being. It is the veterinarian's first duty to ascertain and clinically diagnose whether the dog in question is exhibiting behavior which is properly characterized and described as a type of canine affective aggression behavior. The veterinarian will question the humans or owners of the pet; and may employ a behavioral score sheet chart similar to that illustrated by FIG. 1. It is clearly the practicing veterinarians responsibility to make the determination that the dog in question is exhibiting a type of canine affective aggression behavior rather than an abnormal behavior caused structural brain disease, a biochemical disorder, cognitive dysfunction, or a functional psychosis; and also to identify whether that form is dominance-related aggression, territorial aggression, fear-based aggression, aggression directed toward children, or any other type properly included within affective aggression behaviors. The veterinarian may then choose one or more preferential serotonin reuptake inhibitor compounds as the therapeutic active agent to be administered for modifying the dog's behavior.

A. Preferential/Discriminatory Serotonin Reuptake Inhibitor Compounds

The present behavior modification methodology employs and utilizes a very small group of substituted dibenzazepines for the treatment of canine affective aggression behaviors. As will be described in detail hereinafter, the overwhelming majority of tricyclic antidepressant compositions are unsuitable for use because these are either indiscriminate or non-selective by their overly broad pharmacologic activities, or are not effective in inhibiting serotonin reuptake in meaningful terms. It will be recognized and appreciated therefore that, unlike conventional practices and beliefs to date which hold all the tricyclic antidepressants to be pharmacologically similar and undistinguished in their pharmacokinetic effects, the present treatment method is based and relies upon a formal separation and segregation of the conventionally known tricyclic substituted dibenzazepines into very different and markedly distinguishable categories.

The present method for behavioral modification of canine affective aggression behaviors is expressly limited and restricted to the group consisting of clomipramine, amitriptyline, nortriptyline; their pharmacologically effective metabolites such as demethylclomipramine; and racemic mixtures as well as individual R or S enantiomers of each of these substances. This explicit and limited membership for the category of preferential/discriminatory serotonin reuptake inhibitors is described in detail by Tables 1, 2, and 3 respectively.

TABLE 1

Preferential/Discriminatory Serotonin Reuptake Inhibitors

| Name of Compound | Metabolite(s) | Pharmacokinetic Preparations |
|---|---|---|
| clomipramine | demethylclomipramine | racemic mixtures as well as individual R or S enantiomers |
| amitriptyline | nortriptyline | racemic mixtures as well as individual R or S enantiomers |
| nortriptyline | no effective metabolites | racemic mixtures as well as individual R or S enantiomers |

TABLE 2

| Common Name | Chemical Name | Formula | Ref |
|---|---|---|---|
| clomipramine | 3-chloro-10,11-dihydro-N,N-dimethyl-5H-benzo-[b,f]azepine-5-propamine | (structure with CH₂CH₂CH₂N(CH₃)₂ and Cl) | Craig, et. al., J. Org. Chem. 26: 135 (1961); Swiss patent No. 371,799 |
| amitriptyline | 3-(10,11-Dihydro-5H-dibenzo-[a,d]cyclohepten-5-ylidene-N,N-dimethyl-1-propanamine | (structure with CHCH₂CH₂N(CH₃)₂) | Belgium patent No. 584,011; British Patent Nos. 858,187 858,188 |
| nortriptyline | 3-(10,11-Dihydro-5H-dibenzo[a,d]cyclohepten-5-ylidene)-N-methyl-1-propamine | (structure with CHCH₂CH₂NHCH₃) | U.S. Pat. Nos. 3,922,305 and 3,442,949 |

TABLE 3

Pharmacologic Parameters*

0-none
+-slight
++-moderate
+++-high
++++-very high
+++++-highest

| | Amine Uptakes Blocking Activity | | Half-life (hours) | Therapeutic Plasma Level (ng/ml) | Time to Reach Steady State (days) |
|---|---|---|---|---|---|
| | Norepi-nephrine | Serotonin | | | |
| Tertiary Amines | | | | | |
| Amitriptyline | ++ | ++++ | 31–46 | 110–2501 | 4–10 |
| Clomipramine | ++ | +++++ | 19–37 | 80–100 | 7–14 |
| Secondary Amine | | | | | |
| Nortriptyline | ++ | +++ | 18–44 | 50–150 | 4–19 |

*Drug Facts And Comparisons, 1995, p. 1385.

The most preferred preferential/discriminatory serotonin reuptake inhibitor compound within the narrow category of suitable agents for modifying the behavior of canine affective aggression behaviors is clomipramine or its active metabolite demethylclomipramine. These preferred compounds may be administered as racemic mixtures or as individually purified R or S enantiomers. It will be noted that in recent years the differences and value of employing either racemic mixtures of a composition or purified and separated enantiomers as individual and distinct pharmacological formulations and preparations has become recognized and appreciated [Landoni, M. F. and P. Lees, J. Vet. Pharmacol. Therap. 19: 82–84 (1996); Wright, M. R. and F. Jamali, JPM 29: 1–9 (1993); and the citations listed within these published articles]. For these reasons, the preferred substance includes not only the native clomipramine but also its active metabolite, as well as racemic mixtures and R or S enantiomers of the formulation. Concomitantly, each of the other members in this narrow category of preferential/discriminatory serotonin reuptake inhibitor compounds may also be employed in the original formulation, or the active metabolite as well as racemic mixtures and R or S enantiomer format.

B. Pharmaceutical Formulations, Dose Ranges, And Routes Of Administration

The preferential/discriminatory serotonin reuptake inhibitor compound chosen for use with the veterinary treatment method herein can be administered in any appropriate biocompatible carrier formulation or preparation for either oral or parenteral administration. The chosen compound can be any of those listed by Tables 1, 2, or 3 respectively; and be introduced in-vivo to the recipient dog by any means or routing that substantively causes a clinical modification of canine affective aggression behavior in the subject. Clearly, the dosage to be administered will vary with the particular composition chosen for use, and will vary and be dependent upon the age, general health, and weight of the recipient dog; the kind of concurrent medical treatment, if any; and the severity of the canine affective aggression condition observed or described by the dog's human family members. A summary of the preferred route of administration, the desirable dosage range, the optimal daily dosage, and the expected duration of treatment is given by Table 4 below.

TABLE 4

| Drug | Preferred Routing | Expected Daily Dosage Range (per dog) | Optimal Daily Dosage | Expected Duration of Treatment |
|---|---|---|---|---|
| Clomipramine HCl | per oral/or by injection | 10–400 mg. | 25–300 mg. | 3–4 wks to 5–6 months |
| Amitriptyline HCl | per oral/or by injection | 10–500 mg. | 100–200 mg. | 3–4 wks to 5–6 months |
| Nortriptyline HCl | per oral/or by injection | 20–150 mg. | 75–100 mg. | 3–4 wks to 5–6 months |

Generally, oral administration ("per os") is most preferred; and the appropriate dosage can typically be admixed with the dog's food without major difficulty. Moreover, the typical daily oral dosage will be in the range from 10–500 mg. in total of the chosen preferential/discriminatory reuptake inhibitor compound, given once or perhaps twice daily for several weeks time or for up to 6 months in duration, or even indefinitely in the most severe instances.

Furthermore, although oral administration is most preferred, any means for parenteral administration is also available to the veterinarian. Parenteral administration is most desirably performed by injection into an appropriate site in the animal's body. However, because of the inconvenience and the distress of injection generally, the oral route of administration is to be at least attempted if the dog is eating reasonably well at the time of treatment.

If the preferred clomipramine (or demethylclomipramine) is to be administered as the pharmaceutical agent, the suggested dose schedule for treating a recognized type of canine affective aggression behavior in dogs is desirably about 10–50 mg/kg by mouth once daily for a minimum time period of 3 weeks duration to affect a behavioral change; and a longer duration of 24 months treatment time for a maximum modification of behavior. Treatment may then be continued indefinitely or the dog weaned-off the medication (depending on the success of concurrent behavior modification).

Alternatively, should the necessary route of administration be parenteral, the chosen composition will be prepared in sterile form, available in multiple or single dose formats; and be dispersed in a fluid carrier such as sterile physiological saline or a 5% dextrose solution commonly used with injectables. All of these dosages, schedules, and routes of administration are deemed to be within the scope of the present methodology.

C. Potential Complications, Contradictions, And General Considerations.

The potential complications and side effects of using preferential/discriminatory serotonin reuptake inhibitor compounds include antimuscarinic effects of the drugs, cerebral toxicity and some cardiac toxicity. Clinical consequences of the antimuscarinic effects include dry mouth, epigastric distress, constipation, dizziness, tachycardia, palpitations, blurred vision and urinary retention. Paradoxically, excessive sweating may also occur. If weakness and fatigue are present, these are directly attributable to the central nervous effects of the drugs. However, there are marked individual differences in the type and frequency of these side effects, and these are frequently related to the concentration of the active drug in the blood plasma. As with most other medications generally, if the side effects are minor, they may be dealt with by reducing the dosage of the medication or the frequency of administration; but if the side effects become exceedingly troublesome, then the medication may have to be discontinued permanently, or perhaps another formulation within the permitted category may be substituted.

III. THE OTHER CATEGORIES OF SEROTONIN REUPTAKE AGENTS

It is essential and critical to understand clearly that the present treatment methodology employs a narrow and limited category of compositions and formulations cumulatively and collectively identified as preferential/discriminatory serotonin reuptake inhibitor compounds. The present methodology also identifies for the first time major differences and distinctions among the conventional listings and rankings of drugs, particularly among the recognized membership of the substituted dibenzazepines. In particular, the tricyclic antidepressants conventionally listed as a single group due to the similarities in their chemical structure have been reclassified, separated, and segregated into very different categories on the basis of their individual capacities to react selectively with specific neurotransmitter receptor sites in-vivo. The reclassified categories of different serotonin reuptake agents and the recognized listing of their pharmacologic and pharmacokinetic parameters are given by Tables 5 and 6 respectively below.

TABLE 5

Different Categories of Serotonin Reuptake Agents

Category A: Selective Serotonin Reuptake Inhibitors (SSRIs)

fluoxetine;
paroxetine;
sertraline;
fluvoxamine;
indalpine;
femoxetine;
zimeldine;
trazodone.

Category B: Preferential/Discriminatory Reuptake Inhibitors clomipramine;
demethylclomipramine;
amitriptyline;
nortriptyline.

Category C: Indiscriminate/Non-Selective Serotonin Reuptake Compounds imipramine (a tertiary amine);
desipramine (a secondary amine);
amoxapine (a secondary amine);
protriptyline (a secondary amine);
lofepramine (a secondary amine).

Category D: Ineffective/Non-Efficacious Serotonin Reuptake Substances doxepin (a tertiary amine);
trimipramine (a tertiary amine);
maprotiline (a tetracyclic);
bupropion (an aminoketone).

TABLE 6

Pharmacologic Parameters of the Different Categories*

0 - none
+ - slight
++ - moderate
+++ - high
++++ - very high
+++++ - highest

| | Amine uptakes blocking activity | | | | | |
|---|---|---|---|---|---|---|
| | Nor-epi-nephrine | Sero-tonin | Half-life (hours) | Thera-peutic plasma level (ng/ml) | Time to reach steady state (days) | Dose range (mg/day) |
| Category A: Selective Serotonin Reuptake Inhibitors | | | | | | |
| Fluoxetine | 0/+ | +++++ | 2–9 days[1] | — | 2–4 weeks | 20–80 |
| Paroxetine | 0/+ | +++++ | 10–24 | — | 7–14 | 10–50 |
| Sertraline | 0/+ | +++++ | 1–4[1] | — | 7 | 50–200 |
| Category B: Preferential/Discriminatory Serotonin Reuptake Inhibitors | | | | | | |
| Clomipramine | ++ | +++++ | 19–37 | 80–100 | 7–14 | 25–250 |
| Amitriptyline | ++ | ++++ | 31–46 | 110–250[1] | 4–10 | 50–300 |
| Nortriptyline | ++ | +++ | 18–44 | 50–150 | 4–19 | 30–100 |
| Category C: Indiscriminate/Non-Selective Reuptake Compounds | | | | | | |
| Imipramine | ++[2] | ++++ | 11–25 | 200–350[1] | 2–5 | 30–300 |
| Amoxapine[3] | +++ | ++ | 8[4] | 200–500 | 2–7 | 50–600 |
| Desipramine | ++++ | ++ | 12–24 | 125–300 | 2–11 | 25–300 |
| Protriptyline | ++++ | ++ | 67–89 | 100–200 | 14–19 | 15–60 |

TABLE 6-continued

Pharmacologic Parameters of the Different Categories*

0 - none
+ - slight
++ - moderate
+++ - high
++++ - very high
+++++ - highest

| | Amine uptakes blocking activity | | Half-life (hours) | Thera- peutic plasma level (ng/ml) | Time to reach steady state (days) | Dose range (mg/day) |
|---|---|---|---|---|---|---|
| | Nor- epi- neph- rine | Sero- tonin | | | | |

Category D: Ineffective/Non-Efficacious Serotonin Reuptake Substances

| | | | | | | |
|---|---|---|---|---|---|---|
| Doxepin | + | ++ | 8–24 | 100–200[1] | 2–8 | 25–300 |
| Trimipra- mine | + | + | 7–30 | 180[1] | 2–6 | 50–300 |
| Maprotiline | +++ | 0/+ | 21–25 | 200–300[1] | 6–10 | 50–225 |
| Bupropion[5] | 0/+ | 0/+ | 8–24 | — | 1.5–5 | 200–450 |

[1]Parent compound plus active metabolite.
[2]Via desipramine, the major metabolite.
[3]Also blocks dopamine receptors.
[4]30 hours for major metabolite 8-hydroxyamoxapine.
[5]Inhibits dopamine uptake.
*Drug Facts And Comparisons, 1995, p. 1385.

It will be noted that while Table 5 presents the different categories of agents in a reclassified system based on the selectivity for the serotonin receptor site, it is the data of Table 6 in particular which provides the details which explain the underlying basis and rationale for each of the designated categories themselves. Each designated and identified category represents the ability of a formulated compound not only to interact with the serotonin receptor site in-vivo; but also identifies the concomitant and concurrent effects at the norepinephrine receptor site as well as the dopamine receptors site in certain instances. The reclassification and the setting out of individual categories A, B, C, and D respectively thus orient and present each listed drug or compound in its overall actions; and identify the overall effect and result provided by the individual compound if employed as a serotonin reuptake inhibitor.

In particular, category A lists and identifies the representative compositions which are clearly selective for and react specifically with the serotonin receptor site in-vivo. Note that the individual compositions (such as fluoxetine, paroxetine, and sertraline) are rated and recognized as having the greatest powers for reaction with the serotonin receptor site and provide an amine uptake and blocking activity specifically for the serotonin receptor (Table 6). Note also that there is little or no interaction with the norepinephrine receptor sites in-vivo; no meaningful interaction with dopamine receptors; and that the anticholinergic side effects are minimal and non-existent among all the members constituting this category of agents. Accordingly, this category is termed "selective serotonin reuptake inhibitors", a term which clearly describes their selective capabilities and specifically directed pharmacological properties.

Alternatively, the present invention and treatment methodology intends that a narrow class of preferential and discriminatory serotonin reuptake inhibitors listed by Category B will provide a beneficial and highly desirable result. By the data of Table 6 it is shown that each of these individual agents (clomipramine, amitriptyline, and nortriptyline) are rated as having the highest or very highest activities at the serotonin receptor site in-vivo; and show only a modest or slight interaction and blocking activity at the norepinephrine receptor site. Moreover, none of these formulations are believed to interact meaningfully or block dopamine receptors. The major side effects are noted accordingly and will vary as noted with the choice of the particular formulation employed. All of these compounds are thus preferential and discriminatory agents which seek out and preferentially react with the serotonin receptor site in a discriminating manner; and concurrently show only a limited and moderate to slight activity at the other neurotransmitter receptor sites in-vivo. The pharmacological and pharmacokinetic capabilities of this category of compositions is thus clearly discriminatory; and is clearly preferential in its impact and effect at the serotonin receptor site. For these reasons, this small and limited membership is listed together as a separate and distinct category of compositions intended for therapeutic usage.

In comparison, the other conventionally known antidepressant compounds are so broad in their activities and so indiscriminate in their properties as to be entirely unsuitable for use in modifying the behavior of dogs exhibiting a recognized form of canine affective aggression behaviors. The data given by Table 6 presents two additional groupings, categories C and D respectively, both of which should not be employed and are not desirable for use with the present invention. Category C identifies the indiscriminate/non-selective serotonin reuptake compounds. These include imipramine, amoxapine, desipramine, and protriptyline as well as lofepramine. The data of Table 6 shows that these formulations are moderate or less in their blocking or inhibitory activity at the serotonin receptor site; and concurrently are high to very high in their activity at the norepinephrine receptor sites. Thus, the primary effect is within the norepinelphrine system rather than the serotonin system; and the effects are broadly based and genes as regards serotonin reuptake capabilities. The net result is an indiscriminate and non-selective interaction and effect among the different neurotransmitter receptor systems and an absence of discriminatory power to effect a behavioral modification of meaningful worth.

Finally, the membership of category D is an even more extreme instance of unsuitable and undesirable serotonin reuptake substances. The membership of category D includes doxepin, trimipramine, moprotiline, and bupropion. Note that structurally maprotiline is a tetracyclic composition while bupropion is an aminoketone. The data provided by Table 6 show that each of the formulations listed within category have little or no effective activity at the serotonin receptor site; and each has a varying capability from none to high in the blocking activity at the norepinephrine receptor sites. Some dopamine receptor activity is also identified. In addition to the major side effects for each of the members within category D, it is clear that the entire membership of this category is ineffective and non-efficacious in the ability to act specifically and functionally at the serotonin receptor. Accordingly, these compounds are classified together in one group as being ineffective and unsuitable substances which are to be avoided when practicing the present methodology.

Other Considerations

It will be noted and appreciated that the conventional usage of the tricyclic substituted dibenzazepines has been predominantly used as antidepressants; and occasionally have been employed as sedatives or tranquilizing agents in both human and animal patients. The tricyclic antidepressants also have occasionally been used as hypnotics because of their sedative properties; however, this last usage is very infrequent. Instead, their general use is as an antidepressant and as an agent to promote sleep and reduce excitability in the patient.

These conventionally known uses for the tricyclic dibenzozepines are clearly distinguishable and separate from the present methodology—which is to modify the behavior of dogs exhibiting a recognized form of canine affective aggression behaviors. In addition, conventional pharmacological practice does not separate or distinguish among the individual formulations of the tricyclic antidepressant drugs to any meaningful degree nor for any particular purpose; instead, the commonly accepted view and belief is—that due to the similarity of their chemical structures and uniformity of their pharmacological profiles—there is very little difference among the different members constituting the tricyclic antidepressant family for the purposes of treating depression or providing sedation or tranquilizing effects. In this context, therefore, the very foundations and underlying premises which have conventionally caused pharmacologists to classify the tricyclic antidepressant drugs as a single and uniform alike family—have been broken and removed by the present treatment methodology. Clearly, the present invention presents an entirely unique and uncontemplated reclassification of these drugs into a far more meaningful and distinct reorientation and distinctive categorization unlike anything previously known in the pertinent technical field and scientific literature.

IV. CASE HISTORIES AND INDIVIDUAL DATA

The in-vivo case histories and data provided hereinafter show the use of preferential/discriminatory serotonin reuptake inhibitor compounds for clinical modification of canine effective aggression behaviors. While the case history and in-vivo data presented is limited and employs clomipramine alone for the clinical modification of affective aggression in household dogs, these results and empirical data are direct evidence and probative facts illustrating and proving the general consequences of using this narrow category of preferential compounds clinically to treat each of the different types of canine affective aggression. For these reasons, the case histories and data provided are deemed to exemplify and to represent the pharmacological utility, clinical benefits, and true value for the present invention as defined.

Case History 1

The subject was an Australian Shepherd called "Garp", a 14-year old castrated male dog weighing about 46 pounds. Garp showed affective aggression especially in the presence of other dogs. Initially, Garp was treated with a beta-blocker (inclerol) which only increased his aggressive behavior. After one week on inderal, the beta-blocker treatment was discontinued and clomipramine given at 25 mg daily was administered. After one week's treatment with clomipramine, Garp's human owners noted a slight improvement in his aggressive behavior. Three weeks after initial treatment with clomipramine was started, his owners rated his behavior as 50–75% improvement; and reported that the dog was "doing well, much improved, happier, less aggressive." After several weeks' treatment with clomipramine, the improvement in aggression behavior was maintained. The dog was reported by his owners as having gained weight and otherwise doing well in all respects.

Case History 2

The subject was a Lhasa Apso, 2 years and 8 months in age, and weighed approximately 20 pounds. This dog was clinically diagnosed with the dominance aggression form of affective aggressive behavior and showed some territorial aggression (all varieties of affective aggression). Clomipramine treatment of the dog was begun first at approximately 1 mg/kg twice a day (for one week's duration); and then increased to approximately 2.5 mg/kg given twice a day. After two weeks of clomipramine treatment, the owners rated the dog as "slightly improved" in behavior; and noted that no aggression occurred towards the owner and there was a decrease in the barking at persons the dog didn't like. After four weeks of clomipramine treatment the dog had improved from the rating of "slight improvement" to a "moderately improved" rating. The owners noted a large difference in the dog's behavior; and the improvement in aggressive behavior was sustained through the eight weeks following the termination of clomipramine administration.

Case History 3

The subject was a spayed female German Shepherd, 6.5 years in age, and weighed approximately 62 pounds at the time of clinical examination. This dog had a combination of fear and territorial aggression with affective displays. Treatment was begun with clomipramine given once a day at a dosage slightly less than 1 mg/kg. Moderate improvement in behavior was noted after two weeks' treatment with clomipramine. This moderate improvement in behavior was still evident eight weeks after the initiation of clomipramine therapy when the dog was considered to be "much better" with other dogs. An interim comment was that the dog was more affectionate with the family members; and that there had been no fights with the sisters usually dominant dog when the two dogs were in the family circle.

Case History 4

The subject was a female Cocker Spaniel called "Dutchy", approximately two years old and having a body weight of about 9.7 kilograms at the time of initial examination. The clinical diagnosis was affective aggression behavior which was dominance aggression and/fear aggression. The treatment was clomipramine given orally once daily at a dosage of 25 mg daily. After one week of clomipramine treatment, the owner considered her dog to be about 25–50% improved in behavior. The owner noted that there was no more growling by the dog; and the dog now accepted interventions such as the holding of her feet and putting nail clippers over the dog's nails, which the dog did not previously allow. After two weeks of clomipramine treatment, the owner stated that the dog was still "fine in the house" and still accepting of nail clippers positioned over the dog's nails. However, the dog was noted still to be barking and growling at strangers on the street. After one month's duration of clomipramine treatment, the dog was seen as much calmer on the street; and accepted nail clipping with no aggressive response (no lip curling as had been seen previously The dog also allowed its owner to remove a burr from the foot, another maneuver which had previously elicited aggression towards the owner. After two months of clomipramine treatment, the dog was regarded as being essentially non-aggressive was fine with people on the streets without any aggressive responses. The improvement in behavior was assessed in the 50–75% range. The only reason giver that the improvement was not rated higher was that the dog growled once when a tick was removed from the ear (the only area which now caused the dog any concern). The owner was delighted with this improvement in behavior as a consequence of clomipramine treatment.

Conclusions:

Clomipramine, a representative member of the category of compounds termed "preferential/discriminatory serotonin reuptake inhibitors", is very effective for the treatment of interspecific affective aggression in dogs. Although the case histories as presented were performed in the absence of any behavior modification therapy, it is envisioned that the combination of behavior modification therapy with the administration of preferential/discriminatory serotonin reuptake inhibitor treatment would provide even better results than use of the drug alone. Although the drug treatment method works effectively by itself alone as the case histories indicates it is envisioned that the pharmacologic treatment would provide a more rapid and malleable control of affected dogs and thus increase owner compliance, motivation, and safety over the above that afforded by a behavior modification program alone. In general, it is regarded that this therapeutic treatment for canine affective aggression behaviors will revolutionize the treatment of this condition and reduce the current situation which leads to an overwhelming and unnecessary mortality (estimated at ½–¾ million dogs per year) which are euthanatized because of aggression behavior towards people.

This invention is not to be limited in form nor restricted in scope except by the claims appended hereto.

What I claim is:

1. A veterinary method for clinically modifying the behavior of a household dog exhibiting a type of canine affective aggression, said veterinary behavioral modification method comprising the steps of:
    administering to the household dog exhibiting a type of canine affective aggression behavior an effective amount of at least one preferential serotonin reuptaking inhibitor compound; and
    allowing sufficient time for said administered preferential serotonin reuptake inhibitor compound to modify clinically the canine affective aggression behavior of the household dog.

2. A veterinary method for clinically modifying the behavior of a household dog exhibiting a type of canine affective aggression behavior, said veterinary behavioral modification method comprising the steps of:
    administering to the household dog exhibiting a type of canine affective aggression behavior a first effective amount of at least one preferential serotonin reuptake inhibitor compound; and
    allowing sufficient time for said first administered preferential serotonin reuptake inhibitor compound to begin clinical modification of the canine affective aggression behavior of the household dog; and
    administering at least a second effective amount of said preferential serotonin reuptake inhibitor compound to the household dog to modify clinically further the canine affective aggression behavior of the household dog.

3. The veterinary behavior modification method as recited in claim 1 or 2 wherein said type of canine affective aggression behavior is an interspecies interaction behavior between a household dog and humans.

4. The veterinary behavior modification method as recited in claims 1 or 2 wherein said type of canine affective aggression behavior is a type selected from the I group consisting of dominance-related aggression behaviors, territorial aggression behaviors, fear-based aggression behaviors, and aggression behavior directed towards children.

5. The veterinary behavior modification method as recited in claim 1 or 2 wherein said administered preferential serotonin reuptake inhibitor is a compound selected from the group consisting of clomipramine, amitriptyline, nortriptyline, demethylclomipramine, and racemic mixtures and individual R or S enatiomers of these compounds.

6. The veterinary behavior modification method as recited in claim 1 or 2 wherein said preferential serotonin reuptake inhibitor is administered orally to the household dog.

7. The veterinary behavior modification method as recited in claim 1 or 2 wherein said preferential serotonin reuptake inhibitor is administered parenterally to the household dog.

* * * * *